(12) United States Patent
Metzger-Groom et al.

(10) Patent No.: US 7,114,209 B2
(45) Date of Patent: Oct. 3, 2006

(54) METHOD FOR CLEANING A SOILED ARTICLE

(75) Inventors: Sabine Ursula Metzger-Groom, Morpeth (GB); Colin James Lowery, Newcastle upon Tyne (GB); Michael Duncan, Morpeth (GB)

(73) Assignee: The Procter & Gamble Company, Cincinnati, OH (US)

( * ) Notice: Subject to any disclaimer, the term of this patent is extended or adjusted under 35 U.S.C. 154(b) by 558 days.

(21) Appl. No.: 10/317,788

(22) Filed: Dec. 12, 2002

(65) Prior Publication Data

US 2003/0106164 A1 Jun. 12, 2003

(51) Int. Cl.
*D06F 35/00* (2006.01)
(52) U.S. Cl. .............................. 8/158; 8/159; 68/12.12
(58) Field of Classification Search .................... 8/158, 8/159; 68/12.02; 134/113
See application file for complete search history.

(56) References Cited

U.S. PATENT DOCUMENTS

| | | | |
|---|---|---|---|
| 2,430,668 A * | 11/1947 | Chamberlin | 68/12.02 |
| 5,129,241 A * | 7/1992 | Kiuchi et al. | 68/12.04 |
| 5,241,845 A * | 9/1993 | Ishibashi et al. | 68/12.02 |
| 5,291,626 A | 3/1994 | Molnar et al. | |
| 5,419,163 A | 5/1995 | Kim et al. | |
| 5,438,507 A * | 8/1995 | Kim et al. | 700/1 |
| 5,560,060 A | 10/1996 | Dausch et al. | |
| 5,603,233 A * | 2/1997 | Erickson et al. | 68/12.02 |
| 5,611,867 A | 3/1997 | Cooper et al. | |
| 5,960,804 A | 10/1999 | Cooper et al. | |
| 6,122,840 A * | 9/2000 | Chbat et al. | 34/496 |
| 6,763,687 B1 * | 7/2004 | Jo et al. | 68/12.01 |

FOREIGN PATENT DOCUMENTS

| | | |
|---|---|---|
| DE | DD 214 691 | 10/1984 |
| EP | 0 526 860 B1 | 2/1993 |
| EP | 0 582 329 B1 | 2/1994 |
| EP | 0 589 244 B1 | 3/1994 |
| EP | 0 633 342 B1 | 1/1995 |
| EP | 0 649 933 B1 | 4/1995 |
| EP | 0 725 181 A1 | 8/1996 |
| EP | 1 111 119 A2 | 6/2001 |
| WO | WO 96/21390 | 7/1996 |

* cited by examiner

*Primary Examiner*—Frankie L. Stinson
(74) *Attorney, Agent, or Firm*—David V. Upite; Julia A. Glazer; Kim W. Zerby

(57) ABSTRACT

A method for measuring soil in a wash liquor or other soil-containing liquid medium, the method comprising:

a) a soil sensing step wherein the soil-containing liquid medium is contacted with a plurality of fuzzy-correlated soil-sensing means, each responsive to a distinct physico-chemical soil characteristic and providing one or more soil parameter measurements corresponding thereto;

b) a data processing step wherein the soil parameter measurements for each sensing means are entered as input data into a model algorithm defined on the basis of an algorithm dataset comprising experimental or consumer-generated soil parameter and soil concentration information and which functions to generate predicted soil data of enhanced confidence level; and c) a communication step wherein one or more signals dependent upon the predicted soil data is issued to an output device, data store, user interface, data processor, or an appliance director or module.

The invention also relates to methods for measuring the degree of soiling of a soiled article, and methods for cleaning a soiled article in a wash liquor or other liquid medium.

24 Claims, No Drawings

METHOD FOR CLEANING A SOILED ARTICLE

CROSS REFERENCE TO RELATED APPLICATIONS

This application claims priority under 35 U.S.C. § 119(a) to Great Britain Application Serial No. 0129668.0, filed Dec. 12, 2001.

FIELD OF THE INVENTION

The present invention relates to a method for measuring soil in a wash liquor or other soil-containing liquid medium. The invention also relates to a method for measuring the degree of soiling of a soiled article, and to a method for cleaning a soiled article in a wash liquor or other liquid medium.

BACKGROUND OF THE INVENTION

In recent years there has been considerable activity in the field of so-called 'smart' appliances, i.e., household and other appliances which incorporate sensing systems responsive to one or more process or environmental conditions and which operate under the control of a model algorithm so as, for example, to automate some manual function of the appliance, to economize on energy or reduce environmental impact, to optimise the ease of use and performance of the appliance or of an ancillary product, or to provide some new appliance functionality.

Smart appliance technology is finding particular application in the field of cleaning appliances including automatic laundering, dry-cleaning and dishwashing machines, both domestic and commercial. Typical sensors in use today include water level sensors in clothes washers, humidity sensors for automatic dryer control, temperature sensors, turbidity and other optical sensors for sensing wash water soil, conductivity sensors for sensing water hardness or for detecting the type of product being used, position sensors for applications such as dishwasher spray arm position, speed sensors to detect the rotational speed of the clothes drum, torque, inertia and water absorption sensors for use in load and fabric type sensing, and accelerometers to sense vibration caused by out-of-balance loads in washers.

The accurate and reliable estimation of the level and composition of substrate soil is of especial importance from the viewpoint of determining the correct product usage for achieving optimum cleaning, finishing and fabric care performance. Many consumers will decide on the correct dosage to use based on a visual assessment of the soiled items and in particular on the degree of staining of laundry items. Visual assessment often provides a false impression of the degree of soiling however. A stain may make a big visual impact but it could in practice represent a small soil load. Many common body soils on the other hand have low visibility. So often a consumer will overdose product in cases where the soil load is visible but low; or underdose product in cases where the soil load is of low visibility but high.

There is a need therefore to develop model algorithms that can provide a robust and accurate measurement of the soil load in a soil-containing liquid medium or an accurate prediction of the soil load on the soiled article for use in estimating optimum product usage levels. Soil levels and composition are difficult to measure accurately, however, in part because of their varying origin and complexity. No single parameter currently exists that can directly measure soil since it is a heterogeneous substance composed of a multitude of components having differing physical, chemical and biological properties. Using turbidity as a measure of soil, for example, could lead to an inconclusive or inaccurate assessment of the soil load because turbidity only reflects one aspect of the soil. In addition the properties and environmental history of the soil-containing system, for example the water source, water quality, hardness, substrate load, etc can also affect the measurement process and lead to a less accurate prediction of the soil by, in effect, increasing noise and lowering signal-to-noise ratio.

Another aspect of the problem is that of accurately predicting the substrate soil load prior to the cleaning operation and detergent product delivery. Typically the absolute soil level of the clothes has been determined from the steady state saturation value of a turbidity sensor signal and from the time the turbidity signal takes to reach that value from an initial condition at the start of the wash. Reaching a steady state saturation value can take a significant amount of time, however, and it would clearly be advantageous to determine predicted soil levels by a dynamic process whereby the optimum product usages can be determined prior to achievement of a steady state and prior to delivery of the detergent or ancillary products into the cleaning liquor.

Accordingly the present invention provides improved methods using soil sensor-based model algorithm techniques for measuring the soil load in a soil-containing liquid medium and for estimating the soil load on the soiled article for use in predicting optimum product usage levels and other dosage-related control parameters.

SUMMARY OF THE INVENTION

The present invention relates generally to methods for measuring soil in a wash liquor or other soil-containing liquid medium, methods for measuring the degree of soiling of a soiled article, and methods for cleaning a soiled article in a wash liquor or other liquid medium.

According to a first aspect of the invention, the present invention relates to a method for measuring soil in a wash liquor or other soil-containing liquid medium wherein the method comprises a soil-sensing step, a data processing step and a communication step. In the soil-sensing step, the soil-containing liquid medium is contacted with one or more and preferably with a plurality of soil-sensing means, each responsive to a distinct physico-chemical soil characteristic and providing one or more soil parameter measurements corresponding thereto. Being responsive to distinct characteristics of the soil, the soil-sensing means provide an overlapping but slightly different 'picture' of the soil, a condition which is sometimes referred to herein as 'fuzzy-correlated'.

Thereafter, the soil parameter measurements for each sensing means are entered as input data into a model algorithm and subjected to a data processing step. The model algorithm is defined on the basis of a dataset, herein referred to as 'the algorithm dataset', which comprises experimental or consumer-generated soil parameter and soil concentration information. The function of the model algorithm is to generate predicted soil data of known and/or enhanced confidence level.

In the communication step, one or more signals dependent upon the predicted soil data is issued to an output device, data store, user interface, data processor, or an appliance director or module.

The invention also relates to a method for measuring the degree of soiling of a soiled article wherein the soiled article (which term encompasses a plurality of soiled articles as for instance a laundry or dishwasher load) is subjected to a wetting step in which the soiled article is brought into contact with a liquid medium to initiate removal or partial removal of soil from the soiled article and wherein the resulting soil-containing liquid medium is contacted in a soil-sensing step with one or more and preferably with a plurality of soil-sensing means each responsive to a distinct physico-chemical soil characteristic and providing one or more soil parameter measurements corresponding thereto.

It is a feature of the invention that the methods described herein can provide an accurate prediction of the degree of soiling of the soiled article under partial soil-removal conditions and prior to achieving an equilibrium or steady state. In this context, it is preferred that the soil sensing step be iterated at a plurality of time intervals after the initiation of removal or partial soil removal and prior to the soil-containing liquid medium reaching steady state or otherwise predefined conditions. In the data processing step, the iterated soil parameter measurements are then entered as input data into a model algorithm defined on the basis of an algorithm dataset developed under the predefined conditions and which functions to generate predicted soil data and the confidence level thereof extrapolated to the predefined conditions.

In preferred article-soiling measurement embodiments, the soil-containing liquid medium is contacted with a plurality of fuzzy-correlated soil-sensing means, the soil sensing step being iterated at a plurality of time intervals after the initiation of soil removal and prior to the soil-containing liquid medium reaching a steady state condition. In this case the function of the model algorithm is to generate predicted soil data of enhanced confidence level extrapolated to said predefined conditions.

The present invention also relates to methods for cleaning a soiled article in a wash liquor or other liquid medium. In a preferred aspect, the method comprises a wetting step wherein the soiled article is brought into contact with a liquid medium to initiate removal or partial removal of soil from the soiled article. Suitably the liquid medium can be aqueous or non-aqueous, preferred liquid media including water, organic solvents, silicone solvents, chlorinated solvents and mixtures thereof. The wetting step is preferably undertaken prior to treatment of the soiled article with detergent in cleaning-effective or optimum amounts and is thus sometimes referred to herein as a pre-wetting step. Nevertheless, it will be understood that a certain amount of surfactant or emulsifier compatible with the soil-sensing means can be included in the wetting or pre-wetting liquid medium for promoting the soil-sensing process. The soil-containing liquid medium is then contacted in a soil-sensing step with one or more soil-sensing means, each responsive to a distinct physico-chemical soil characteristic and providing one or more soil parameter measurements corresponding thereto. The soil parameter measurements thus generated are then entered as input data into the model algorithm which functions to generate predicted soil data and the confidence level thereof, and one or more signals dependent upon the predicted soil data is issued to an output device, data store, user interface, data processor or an appliance director or module.

Thereafter the soiled article is treated in a cleaning step with one or more detergent products in amounts effective for cleaning the soiled article. Dosage-related control parameters for the cleaning step, parameters such as the type or the amount of product to be delivered, are determined preferably prior to treatment in accord with the predicted soil data. Optionally, the article is thereafter treated in a finishing step with one or more finishing aids.

Again in preferred cleaning method embodiments, the soil-containing liquid medium is contacted with a plurality of fuzzy-correlated soil-sensing means, each responsive to a distinct physico-chemical soil characteristic, and the model algorithm functions to generate predicted soil data of enhanced confidence level relative to the data generated by the individual soil-sensing means. Preferably also the soil sensing step is iterated at a plurality of time intervals after the initiation of soil removal and prior to treatment of the soiled article with cleaning-effective or optimum amounts of detergent, the algorithm dataset comprises soil parameter and soil concentration information developed under predefined, preferably steady state conditions, and the model algorithm functions to generate predicted soil data and the confidence level thereof extrapolated to said predefined conditions.

In addition to experimental and consumer-generated soil parameter and soil concentration information, the algorithm dataset of the model algorithm preferably comprises recommended usage data which is specific to one or more products against which the model algorithm has been developed and on the basis of which the model algorithm functions to generate one or more optimum dosage-related parameters such as optimum product usage and/or predicted soil data. Such model algorithms are said herein to be product-specific.

By 'recommended usage data' is meant the data or instructions (or one or more parameters derived therefrom) supplied by the manufacturer relating to the use of his product, for example the recommended product usages for given soil loads and water hardness or for given types of articles to be cleaned. By 'optimum dosage-related parameter' is meant a dosage-related parameter, for example, the type of product, product usage, predicted soil data and the like, which is a best fit to the algorithm model for the particular product task. The term 'optimum product usage data' is construed similarly.

A broad range of physico-chemical soil parameters and corresponding sensing means can be applied in the methods of the invention, but preferred soil parameters include turbidity, conductivity, pH, surface-tension, refractive index, ionic strength, heat capacity, viscosity, thermal conductivity, coefficient of expansion, dipole moment, adsorption, density, hydrophobicity, optical density, osmosis, optical activity, water-hardness and combinations thereof. The selection of suitable sensing means will depend largely upon the composition and origin of the soil. As discussed above, soil is a highly heterogeneous mixture of soil types including greasy/oily, particulate, enzyme-sensitive, bleachable soils, burnt- and baked-on soils, etc. Soil categories in terms of origin can be equally diverse, including for example body soils, environmental soils from smoke, grass, etc, incidental soils including food stains etc, applied soils from cosmetics, haircare products, etc, cooking soils, etc. Highly preferred herein for efficacy across a broad spectrum of soil types and categories is the combination of turbidity and conductivity, though it will be understood that these can be supplemented by sensors for other soil parameters as appropriate for the particular cleaning task, soil types and soil categories, or indeed to combinations of soil parameters other than turbidity and conductivity. Preferably however, the sensing means will be fuzzy-correlated in the sense that they are responsive to different physico-chemical aspects of the soil and will together be predictive of the soil load in the wash liquor or other liquid medium or on the soiled article with enhanced confidence and accuracy. To this end, the sensor combinations will preferably have one or more pair-wise correlation coefficients in the range from about 0.05 to about 0.95, preferably from about 0.1 to about 0.85, more preferably from about 0.15 to about 0.75. In basis vector model embodiments of the invention, however, the pair-wise correlation coefficients are preferably below about 0.5, more preferably below about 0.3 and can be as low as about 0.05 or even 0 (i.e. fully non-correlated).

Thus according to a preferred aspect of the invention, there is provided a method for measuring the degree of soiling of a soiled article or for cleaning the soiled article in a wash liquor or other liquid medium, the method comprising:

a) a wetting step wherein the soiled article is brought into contact with a liquid medium to initiate removal of soil from the soiled article;
 b) a soil sensing step wherein the soil-containing liquid medium is contacted with a plurality of soil-sensing means each responsive to a distinct physico-chemical soil characteristic and providing one or more soil parameter measurements corresponding thereto, said plurality of soil sensing means including at least a conductivity-based sensor and a turbidity-based sensor;
 c) a data processing step wherein the soil parameter measurements for each sensing means are entered as input data into a model algorithm which functions to generate predicted soil data of enhanced confidence level;
 d) a communication step wherein one or more signals dependent upon the predicted soil data is issued to an output device, data store, user interface, data processor or an appliance director or module; and optionally
 e) a cleaning step wherein the soiled article is treated with one or more detergent products of a type or amount determined prior to treatment in accord with the predicted soil data.

The model algorithm applied according to the invention can be a linear regression model, a non-linear regression model, a fuzzy logic model, a neural network model, a neuro-fuzzy network model, a basis vector model or other known algorithm models. In one preferred embodiment, however, the algorithm is a regression model defined on the basis of one or more regression equations relating the experimental or consumer-generated soil parameter information to known soil concentration levels and which provides best-fit estimates of regression coefficients and corresponding probability distribution functions. Most preferred is a linear regression model method wherein the one or more regression equations of soil parameter on soil concentration is linear or linearizable by appropriate transformation. Preferably the standard deviation for the regression coefficient should be less than about 60%, more preferably less than about 40%, a target which can be achieved by suitable screening and selection of the soil-sensing means. Also highly preferred herein is a so-called basis vector model, details of which are given below.

As a default, the algorithm will normally comprise soil parameter and concentration information that has been previously generated in suitable laboratory experiments, for example by extraction of soil from real consumer loads in a laundry washing machine under predefined conditions, for example conditions corresponding to the achievement of an equilibrium or steady state during the wetting step, or conditions corresponding to a defined extraction period (for example from 5 to 15 minutes) or to a defined amount of soil to be extracted, such conditions being selected according to the requirements of the soil sensing step. The algorithm dataset can be supplemented however by input or output data generated in-vivo, such in-vivo data being sometimes referred to herein as 'consumer-generated'. Supplementing the dataset in this way is valuable for changing the boundary conditions or otherwise reoptimising the model algorithm as explained in detail below. Alternately, it can be valuable for generating a model algorithm that is specific to an individual user or a group of users.

Model Algorithms

A preferred model algorithm for use in the methods of the invention is described below. The algorithm makes use of soil parameter data obtained by extraction of soil under predefined conditions as a basis for determining optimum soil categories and product dosages, by comparing the extracted soil data against a dataset of experimental and/or consumer-generated soil parameter and concentration information.

Algorithm Datasets

In preferred embodiments, the algorithm dataset generally comprises a soil concentration dataset s and one or more experimental or consumer-generated soil parameter datasets, p, q, etc for each sensing means (lower case letters herein indicating measured as opposed to predicted values and bold highlighting being used to indicate algorithm datasets). Thus p, q, s represent algorithm datasets of size k such that for each measured soil value $s_1$, there exists a corresponding measured parameter value $p_i$, $q_i$. In other words:

$$\mathbf{p} = p_1, p_2, \ldots p_i, \ldots p_k$$

$$\mathbf{q} = q_1, q_2, \ldots q_i, \ldots q_k$$

$$\mathbf{s} = s_1, s_2, \ldots s_i, \ldots s_k$$

Corresponding dataset values of the parameters under soil-free conditions are denoted herein as $p^0$, $q^0$ etc. These in turn are used to define so-called offset soil parameter datasets:

$$\mathbf{p}-\mathbf{p}^0 = p_1-p_1^0, p_2-p_2^0, \ldots p_i-p_i^0, \ldots p_k-p_k^0$$

$$\mathbf{q}-\mathbf{q}^0 = q_1-q_1^0, q_2-q_2^0, \ldots q_i-q_i^0, \ldots q_k-q_k^0$$

Normalised Datasets

The algorithm datasets herein are preferably subjected to a normalisation process wherein the data is converted into dimensionless form by normalising against the maximum values of soil parameter or concentration in the dataset as determined in the laboratory or encountered in previous consumer practice. The process of normalisation has been found to be valuable herein for providing more accurate prediction of soil under heavy soil load conditions.

Specifically, the maximum value of soil parameter in the offset soil parameter dataset is denoted herein by $(\mathbf{p}-\mathbf{p}^0)_{max}$, $(\mathbf{q}-\mathbf{q}^0)_{max}$ etc, abbreviated herein to $\mathbf{p}_{max}$ and $\mathbf{q}_{max}$ respectively. The maximum value, $\mathbf{p}_{max}$, etc is defined as the upper n %-ile value of $(\mathbf{p}-\mathbf{p}^0)$ in the corresponding offset soil parameter dataset, wherein n lies in the range from about 80 to about 99, preferably from about 90 to about 98, and most preferably about 95.

The maximum values $p_{max}$, $q_{max}$ are then used to define so-called normalised soil parameter datasets $p''$, $q''$ etc:

$$p''=(p-p^0)/p_{max}=(p_1-p_1^0)/p_{max}, (p_2-p_2^0)/p_{max}, \ldots$$
$$(p_i-p_i^0)/p_{max}, \ldots (p_k-p_k^0)/p_{max}$$

$$q''=(q-q^0)/q_{max}=(q_1-q_1^0)/q_{max}, (q_2-q_2^0)/q_{max}, \ldots$$
$$(q_i-q_i^0)/q_{max}, \ldots (q_k-q_k^0)/q_{max}$$

In a similar way, the maximum value of soil concentration in the algorithm dataset, $s_{max}$, is defined as the upper n %-ile value of soil concentration in the dataset, wherein n lies in the range from about 80 to about 99, preferably from about 90 to about 98, and most preferably about 95. The normalised soil concentration dataset $s''$ is then defined as:

$$s''=s/s_{max}=s_1/s_{max}, s_2/s_{max}, \ldots s_i/s_{max}, \ldots s_k/s_{max}$$

The values $p_{max}$, $q_{max}$, $s_{max}$ etc are sometimes referred to herein as 'boundary conditions'. The boundary conditions play a role in the later application of the algorithm for testing whether the algorithm requires reoptimisation in the light of any new input data.

Soil Category Bands

A number of discrete soil category bands ($s_\mu$) and normalised soil category bands ($s_\mu''$) are thereafter defined based on the maximum value of soil concentration $s_{max}$ in the dataset, wherein (equations 1):

$$s_\mu=s_\mu'' \cdot s_{max} \text{ and } s_\mu''=\delta_\mu(s'')$$

In the above, index $\mu$ is the category band label and $\delta_\mu(s'')$ is a step function having the value 1 within a range of normalised soil concentrations defined for $\mu$ and the value 0 outside the range. Preferably the category bands are defined on the basis of the manufacturer's product-specific recommended usage data, so that for example there could be four bands corresponding to light (L), normal (N), heavy (H) and very heavy (VH) soil loads, the $\mu$ being defined accordingly. Preferably in this case, L corresponds to the normalised soil concentration range from 0 to 0.25, N from 0.25 to 0.5, H from 0.5 to 1.0, and VH greater than 1.0.

Linear Regression Model

In the preferred linear regression algorithms, the soil concentrations and soil parameters are related as follow (equations 2):

$$s=m_p(p-p^0)$$

$$s=m_q(q-q^0)$$

wherein $m_p$ and $m_q$ are regression coefficients having standard deviations $\sigma_p$ and $\sigma_q$.

The normalised soil concentrations and soil parameters on the other hand are related as follows (equations 3):

$$s''=m_p'' p''$$

$$s''=m_q'' q''$$

where $m_p''$ and $m_q''$ are the regression coefficients for the normalised equations with average values of 1 and standard deviations equal to those of the unnormalised equations, $\sigma_p$ and $\sigma_q$.

Using the linear regression model, the soil category bands can also be expressed in normalised parameter form $s_{p,\mu}''$, $s_{q,\mu}''$ etc, wherein (equation 4)

$$s_{p,\mu}''=s_\mu/(m_p \cdot p_{max})$$

Algorithm Input Data

Similar to the treatment of the algorithm datasets, the soil parameter measurement data for which corresponding soil concentration values are to be computed (sometimes referred to herein as the algorithm input data and designated herein as $p_j$, $q_j$ etc) are offset with corresponding measurements of the liquid medium under soil-free conditions, $p_j^0$, $q_j^0$ etc to provide offset soil parameter measurements ($p_j-p_j^0$), ($q_j-q_j^0$) etc. Normalised input data $p_j''$, $q_j''$ are also similarly defined as $(p_j-p_j^0)/p_{max}$, $(q_j-q_j^0)/q_{max}$ etc.

As an initial test the normalised input data is checked against the boundary conditions $p_{max}$, $q_{max}$, etc to see if the data is consistently outside or at the low end of the normalised parameter range. If so, the boundary conditions are recomputed to reflect the new conditions.

Predicted Soil Probability Distributions

The predicted soil probability distributions corresponding to algorithm input data $p_j$, $q_j$ etc are indicated herein by the upper case variable $S_{p,j}$, $S_{q,j}$ etc with normalised predicted soil probability distributions being indicated as before with the suffix n. The overall predicted soil probability distribution ($S_j''$ or $S_j$) is then computed by taking a weighted average of the individual parameter-determined quantities. Corresponding to equations 2 and 3 above, the predicted soil probability distributions can be determined by two approaches, the first based on the distribution for $m_p$ and $s_{max}$ (equation 5):

$$S_j''=\Sigma w_p S_{p,j}/(s_{max} \cdot \Sigma w_p)=[\Sigma w_p m_p(p_j-p_j^0)]/s_{max} \cdot \Sigma w_p$$

and the second based on the distribution for $m_p''$ and the normalised soil parameters (effectively $p_{max}$) (equation 6):

$$S_j''=\Sigma w_p S_{p,j}''/\Sigma w_p=[\Sigma w_p m_p'' p_j'']/\Sigma w_p$$

In the above the summation is taken over the different soil parameters and $w_p$ is a weighting term which is normally taken to be 1. Preferably both equations 5 and 6 are applied and the final result obtained by averaging.

Optimum Soil Category

The overall optimum soil category is indicated herein as $C_j$ and is determined by computing the individual category band functions $C_{\mu,j}$ followed by making a selection decision between the bands. The $C_{\mu,j}$ are determined by computing an overlap function between the predicted soil probability functions and the soil category bands for each soil parameter and then, as above, taking a weighted average of the individual parameter-determined quantities. Again, as above, the $C_{\mu,j}$ can be determined using two approaches, the first based on $m_p$, $s_{max}$ and $s_\mu''$:

$$C_{\mu,j}=\Sigma w_p f(S_{p,j}, s_\mu'')/(s_{max} \cdot \Sigma w_p)$$

and the second based on the $m_p''$, the normalised soil parameters ($p_{max}$) and $s_{p,\mu}''$:

$$C_{\mu,j}=\Sigma w_p f(S_{p,j}'', s_{p,\mu}'')/\Sigma w_p$$

The first equation is referred to herein as equation 7; the second as equation 8. Preferably both equations 7 and 8 are applied and the final result obtained by averaging. In the above, the overlap function f can take any convenient form providing it achieves the function of assigning a portion of the soil probability distribution to each of the various soil category bands in amounts dependent on the degree of overlap between the predicted soil probability function and the soil category bands. Thereafter a selection decision between the individual soil category bands is made either by selecting the band with the largest $C_{\mu,j}$ or, if borderline, selecting the next higher category band.

Optimum Product Dosage

The optimum product dosage is thereafter determined on the basis of the optimum soil category, the water hardness of the feed liquor and the manufacturer's recommended usage data.

Confidence Values

The confidence value of the algorithm is a measure of the success of the algorithm in predicting soil data or soil categories and can be determined in various ways. For example, one measure is the spread in the difference ($\Delta$) between actual ($s_j$) and algorithm-predicted soil levels (av ($S_j$)) over a set of test samples, none of which is in the algorithm dataset. Suitable measures of the spread include, for example, the variance or the mean square of $\Delta$. The algorithm will demonstrate enhanced predictability if the spread is significantly less for multiple sensors than for single sensors.

Another measure of predictability is the overlap between the predicted soil probability distribution and the actual or analytically-determined soil category band. The algorithm will demonstrate enhanced predictability if the overlap is significantly greater for multiple sensors than for single sensors.

Basis Vector Model

The basis vector model is particularly suitable in the case of soil sensors that have a relatively low degree of correlation (for example pair-wise correlation coefficients below about 0.5, preferably below about 0.3) such as conductivity- and turbidity-based sensors. In these circumstances it has been found that the soil composition can be represented with considerable accuracy and reproducibility as a linear combination of soil fractions (sometimes referred to herein as p-soil components) associated with the individual soil sensor types, for example, 'conductive' soil or 'turbid' soil respectively. In effect, the p-soil components act as a 'basis set' of soils that span the overall soil 'vector space'. For this reason, the model is sometimes referred to herein as the 'basis vector' model. By preparing reference standards for different 'pure' p-soils (for example pure sodium chloride in the case of conductive soil), the soil parameter/concentration relationship for each p-soil reference standard can be determined so that in any given instance the actual soil can be said to 'contain' a certain proportion of the reference standard soil. Then knowing the average amounts of the different p-soil components that can be extracted relative to the total soil introduced by the soiled articles (information obtained empirically from previous experimental and consumer-generated data), the model makes it possible to determine the composition of the extracted soil in terms of p-soil components and to obtain a direct estimate of the total soil, its composition, and the optimum product dosage and operating conditions for laundering or cleaning the soiled articles.

Let $S_j^T$ represent the predicted total soil (absolute weight), V represent the volume of wash liquor, $\epsilon_p$ represent the fraction (i.e. percentage/100) of p-soil component extracted on average from the soiled articles (i.e. the p-soil extraction coefficient), $\kappa_{p,j}$ represent the fraction (i.e. percentage/100) of p-soil in the extracted soil, and $m_{p\text{-}soil}$ represent the soil parameter corresponding to 1 g/liter of p-soil reference standard, then, following equation 5, the predicted total soil is defined as follows (equation 9):

$$S_j^T = \Sigma V(w_p/\epsilon_p \kappa_{p,j}) S_{p\text{-}soil,j}/\Sigma w_p$$

wherein the $S_{p\text{-}soil,j}$ are the concentrations of extracted p-soil and are defined, following equation 5, by the relations (equation 10):

$$S_{p\text{-}soil,j} = m_{p\text{-}soil}(p_j - p_j^0), \text{ etc.}$$

Gathering equations 9 and 10 together gives the following equation for predicted total soil (equation 11):

$$S_j^T = \Sigma V(w_p/\epsilon_p \kappa_{p,j}) m_{p\text{-}soil}(p_j - p_j^0)/\Sigma w_p$$

The fraction of p-soil in the extracted soil, $\kappa_{p,j}$ on the other hand is defined by (equation 12):

$$\kappa_{p,j} = m_{p\text{-}soil}(p_j - p_j^0)/\Sigma m_{p\text{-}soil}(p_j - p_j^0)$$

Solution of the two equations, 11 and 12 provides the composition of the extracted soil in terms of the p-soil reference standards as well as the total predicted soil. Once again, the optimum product dosage is thereafter determined on the basis of the total predicted soil, the water hardness of the feed liquor (which can be determined by conductivity) and the manufacturer's recommended usage data. The information on soil load and composition can also be used to control by means of signals issued to an appliance director or module, other wash process parameters including the selection of washing product from an inventory of washing products provided to the user, the order of use of multiple washing products, the duration of washing using one or more products, the temperature or degree of agitation of the wash water, the number of rinses, etc.

The confidence value for the model can be determined in a similar way to the regression model, for example by calculating the spread in the difference ($\Delta$) between actual and algorithm-predicted soil levels over a set of test samples. Suitable measures of the spread include, for example, the variance or the mean square of $\Delta$. The algorithm will demonstrate enhanced predictability if the spread is significantly less for multiple sensors than for single sensors.

Conductivity/Turbidity Basis Vector Model

A basis vector model particularly suitable for use herein employs a combination of conductivity- and turbidity based sensors for detecting and measuring soil. In this instance, the soil composition is represented as a combination of a conductive soil fraction (c-soil) and a turbid soil fraction (t-soil) with offset soil parameter measurements denoted by $(c_j - c_j^0)$ and $(t_j - t_j^0)$ and with corresponding parameters $\kappa_{c,j}$ and $\kappa_{t,j}$ specifying the composition of the extracted soil (equations 13 and 14):

$$\kappa_{c,j} = m_{c\text{-}soil}(c_j - c_j^0)/[m_{c\text{-}soil}(c_j - c_j^0) + m_{t\text{-}soil}(t_j - t_j^0)]$$

$$\kappa_{t,j} = m_{t\text{-}soil}(t_j - t_j^0)/[m_{c\text{-}soil}(c_j - c_j^0) + m_{t\text{-}soil}(t_j - t_j^0)]$$

Suitable conductivity- and turbidity-based sensors include any commercially-available sensors known for use in domestic and industrial household appliances, medical devices or other industrial or scientific applications, suitable examples including in the case of conductivity sensors an Oakton Series 100 Conductivity controller equipped with a Cole Palmer electrode 800-323-4340, and in the case of turbidity sensors a Honeywell X113745-AP or X114325-AP. The conductivity sensor is also used to provide an estimate of water hardness necessary for determining optimum product dosages. Suitable reference standards include, in the case of c-soil, a 1 g/liter aqueous solution of pure sodium chloride, and in the case of t-soil, a 1 g/liter aqueous dispersion of starch. Alternatively, reference standards can be prepared by extracting the total soil from a representative population of consumer-generated soiled articles, separating the total soil into t-soil and c-soil fractions using a suitable solvent or series of solvents, for example water, ethanol, hexanol, etc, and re-dissolving or dispersing the fractions in water at 1% by weight. In this way, reference standards can be prepared which are representative of the entire population of soiled articles against which the manufacturer has developed his recommended usage data.

The ratio of $\kappa_{t,j}:\kappa_{c,j}$ (and of $(t_j-t_j^o):(c_j-c_j^o)$ which differs only to the extent of a proportionality factor and is referred to herein as the T/C ratio) has been found to depend sensitively on the nature and origin (including geographical origin) of the soil or stain type so that each soil or stain type can be said to have its own characteristic 'fingerprint' spectrum based on its averaged $\kappa_{t,j}:\kappa_{c,j}$ or T/C ratio. By comparing measured values of $\kappa_{t,j}:\kappa_{c,j}$ or T/C ratios (or generally of a function dependent upon measured turbidity and conductivity proportionality data) against a dataset of experimental or consumer-generated proportionality data, the predicted soil data can therefore be used to control by means of signals issued to an appliance director or module, various wash process parameters including optimum product dosage information, the selection of washing product from an inventory of washing products provided to the user, the order of use and/or relative amounts of multiple washing products, the duration of washing using one or more products, the temperature or degree of agitation of the wash water, the number of rinses, etc.

In view of the above, preferred model algorithms for use herein can be characterised by having one or more, preferably two or more and more preferably three of more of the following features:

a) the model algorithm is developed using a plurality of fuzzy-correlated soil sensing means having one or more pair-wise correlation coefficients in the range from about 0.05 to about 0.95, preferably from about 0.1 to about 0.85, more preferably from about 0.15 to about 0.75;

b) the model algorithm is developed using a plurality of soil sensing means appropriate to a heterogeneous mixture of soils of different types including greasy/oily, particulate, enzyme-sensitive, bleachable soils, burnt- and baked-on soils, etc or a mixture of soils from different categories including body soils, environmental soils from smoke, grass, etc, incidental soils including food stains etc, applied soils from cosmetics, haircare products, etc, cooking soils, etc.

c) the model algorithm is developed using a combination of turbidity-based and conductivity-based soil sensors;

d) the model algorithm is a linear regression model, a non-linear regression model, a fuzzy logic model, a neural network model, a neuro-fuzzy network model, or a basis vector model;

e) the model algorithm is a regression model defined on the basis of one or more regression equations relating the experimental or consumer-generated soil parameter information to known soil concentration levels and providing best-fit estimates of regression coefficients and corresponding probability distribution functions;

f) the model algorithm is a regression model developed using a plurality of soil sensing means and being defined on the basis of a plurality of regression equations, one or more for each soil-sensing means;

g) the model algorithm is a regression model defined on the basis of one or more regression equations of soil parameter on soil concentration and which is linear or linearizable by appropriate transformation with a standard deviation for the regression coefficient of less than about 60%, preferably less than about 40%;

h) the model algorithm is at least partly defined on the basis of one or more experimental or consumer-generated soil parameter datasets, p, q, etc, at least one for each sensing means, which has been transformed by offsetting with corresponding measurements under soil-free conditions $p^o$, $q^o$, etc so to provide offset soil parameter datasets $(p-p^o)$, $(q-q^o)$, etc;

i) the model algorithm is at least partly defined on the basis of one or more experimental or consumer-generated soil parameter datasets, p, q, etc, at least one for each sensing means, which has been transformed by offsetting with corresponding measurements under soil-free conditions $p^o$, $q^o$ etc so to provide offset soil parameter datasets $(p-p^o)$, etc and wherein the soil parameter dataset is further transformed by normalizing the offset soil parameter dataset $(p-p^o)$, etc against the maximum value of experimental or consumer-generated soil parameter measurements, $p_{max}$ etc in the corresponding offset soil parameter dataset so as to provide the normalized soil parameter dataset $p''$, $q''$ etc, where $p''=(p-p^o)/p_{max}$ and $p_{max}$ is the upper n %-ile value of $(p-p^o)$ in the corresponding offset soil parameter dataset and n lies in the range from about 80 to about 99, preferably from about 90 to about 98, more preferably about 95;

j) the model algorithm is defined on the basis of a plurality of soil parameter datasets, p, q, etc, one for each soil-sensing means;

k) the model algorithm transforms the soil parameter measurement input data for the or each sensing means, $p_j$, $q_j$ etc by offsetting with corresponding measurements of the liquid medium under soil-free conditions, $p_j^o$, $q_j^o$ etc to provide offset soil parameter measurements $(p_j-p_j^o)$, $(q_j-q_j^o)$ etc;

l) the model algorithm transforms the soil parameter measurement input data for the or each sensing means, $p_j$, $q_j$ etc by offsetting with corresponding measurements of the liquid medium under soil-free conditions, $p_j^o$, $q_j^o$ etc to provide offset soil parameter measurements $(p_j-p_j^o)$ etc and further transforms the soil parameter measurement input data by normalizing the offset soil parameter measurements $(p_j-p_j^o)$ etc against the maximum value of experimental or consumer-generated soil parameter measurements $p_{max}$ in the corresponding offset soil parameter dataset so as to generate normalised soil parameter measurements $p_j''$, $q_j''$ etc;

m) the model algorithm is a linear regression model and generates a predicted soil probability distribution on the basis of 1) the soil parameter input data, the soil concentration versus soil parameter regression coefficients $(m_p)$ and the maximum value of soil concentration $s_{max}$ in the algorithm dataset, $s_{max}$ being the upper n %-ile value of soil concentration in the algorithm dataset wherein n lies in the range from about 80 to about 99, preferably from about 90 to about 98, more preferably about 95; and/or 2) the normalised regression coefficients $(m_p'')$, $p_{max}$ and the normalised soil parameter measurements $(p_j'')$, the predicted soil probability distribution being a sum or weighted sum of terms in respect of each soil parameter;

n) the model algorithm undertakes a soil category decision step wherein the soil in the liquid medium is assigned to an optimum one of a plurality of discrete soil category bands on the basis of the predicted soil probability distributions for the or each soil sensing means;

o) the model algorithm undertakes a soil category decision step wherein the soil in the liquid medium is assigned to an optimum one of a plurality of discrete soil category bands defined on the basis of the maximum value of soil concentration $s_{max}$ in the algorithm dataset and product-specific recommended usage data;

p) the model algorithm undertakes a soil category decision step wherein the soil in the liquid medium is assigned to an optimum one of a plurality of discrete soil category bands, the optimum soil category band being assigned on the basis of one or more overlap functions between 1) the predicted soil probability distributions ($S_{p,j}$, $S_{q,j}$ etc) for each soil sensing means and the normalised soil category bands ($s_\mu''$); and/or 2) the normalised predicted soil probability distributions ($S_{p,j}''$, $S_{q,j}''$ etc) for each soil sensing means and the soil category bands expressed in normalised parameter form ($s_{p,\mu}''$, $s_{q,\mu}''$ etc), the optimum soil category being a sum or weighted sum of the overlap functions in respect of each soil parameter.

q) the model algorithm is a basis vector model wherein the predicted soil data is represented as a linear combination of soil fractions each associated with a corresponding soil-sensing means and defined by reference to a standard model soil and wherein the soil fractions are combined in relative proportions dependent upon one or more weighting factors including the measured concentration of the soil fraction in the wash liquor or other liquid medium ($\kappa_{p,j}$); and r) the model algorithm is a basis vector model wherein the predicted soil data is represented by a linear combination of soil fractions including one fraction associated with a conductivity-based sensor (c-soil) and one fraction associated with a turbidity-based sensor (t-soil) with weighting factors dependent upon the measured concentrations of c-soil ($\kappa_{c,j}$) and t-soil ($\kappa_{t,j}$) in the wash liquor or other liquid medium, and wherein preferably the method includes the step of issuing one or more signals dependent upon one or more of $\kappa_{c,j}$, $\kappa_{t,j}$, $\kappa_{c,j}$:$\kappa_{t,j}$, T/C or some other function dependent upon turbidity/conductivity proportionality, to an output device, data store, user interface, data processor, or an appliance director or module for purposes of controlling a cleaning or washing process, wherein T is the offset soil parameter measurement for the turbidity-based sensor ($t_j - t_j^0$) and C is the offset conductivity soil parameter measurement for the conductivity-based sensor ($c_j - c_j^0$).

In preferred embodiments, the model algorithm is characterised by having one or more of the features a), b), c), f), g), h), i), j), k), l), m), n) o) p), q) or r), more preferred being model algorithms characterized by one or more of the features a), b), c), f), g), j), m) o), p), q) or r). Especially preferred are model algorithms characterized by having five or more, preferably 10 or more, and more preferably all of features a) to p) and model algorithms having features a) to d) in combination with features q) and r).

In use a data processing module can be provided for processing the model algorithm for purposes of measuring soil or for cleaning a soiled article in a wash liquor or other liquid medium. The model algorithm will usually be resident as a set of executable instructions or neural network connections in the data processing module; alternatively it can be resident in local, server or network memory. As described hereinabove, input data for the model algorithm comprises one or more soil parameter measurements generated using one or more soil-sensing means, each responsive to a distinct physico-chemical soil characteristic. Output data from the model algorithm on the other hand comprises predicted soil data and the confidence level thereof and/or optimum product usage data. The model algorithm itself is defined on the basis of an algorithm dataset comprising experimental or consumer-generated soil parameter and soil concentration information as described in detail above.

In preferred embodiments, the model algorithm resides as a set of executable instructions or neural network connections in a microprocessor- or neural network-based data processing module with input and output signals corresponding to the algorithm input and output data as described. Moreover, the algorithm input or output data can itself be stored either in the data processing module or in local, server or network memory for the purpose of updating and reoptimising the model algorithm or for generating a user-specific, group-specific or global model algorithm.

What is claimed is:

1. A method for measuring a degree of soiling of a soiled article, the method comprising:
   a) a wetting step wherein the soiled article is brought into contact with a liquid medium to initiate removal of soil from the soiled article;
   b) a soil sensing step wherein the soil-containing liquid medium is contacted with a plurality of soil-sensing means each responsive to a distinct physico-chemical soil characteristic and providing one or more soil parameter measurements corresponding thereto; wherein the soil sensing step is iterated at a plurality of time intervals after the initiation of soil removal and prior to the soil-containing liquid medium reaching steady state or otherwise predefined conditions, and wherein the model algorithm is defined on the basis of an algorithm dataset developed under said predefined conditions and functions to generate predicted soil data and the confidence level thereof extrapolated to said predefined conditions;
   c) a data processing step wherein the soil parameter measurements for each sensing means are entered as input data into a model algorithm defined on the basis of an algorithm dataset comprising experimental or consumer-generated soil parameter and soil concentration information and which functions to generate predicted soil data of enhanced confidence level; and
   d) a communication step wherein one or more signals dependent upon the predicted soil data is issued to an output device, data store, user interface, data processor or an appliance director or module.

2. A method for cleaning a soiled article in a liquid medium, the method comprising;
   a) a wetting step wherein the soiled article is brought into contact with a liquid medium to initiate removal of soil from the soiled article;
   b) a soil sensing step wherein the soil-containing liquid medium is contacted with a plurality of soil-sensing means each responsive to a distinct physico-chemical soil characteristic and providing one or more soil parameter measurements corresponding thereto;
   c) a data processing step wherein the soil parameter measurements are entered as input data into a model algorithm defined on the basis of an algorithm dataset comprising experimental or consumer-generated soil parameter and soil concentration information and which functions to generate predicted soil data of enhanced confidence level;
   d) a communication step wherein one or more signals dependent upon the predicted soil data is issued to an output device, data store, user interface, data processor or an appliance director or module; and e) a cleaning step wherein the soiled article is treated with one or more detergent products of a type or amount determined prior to treatment in accord with the predicted soil data.

3. A method according to claim 2 wherein the algorithm dataset additionally comprises product-specific recommended usage data and the model algorithm functions to generate predicted soil data and/or optimum product usage data.

4. A method according to claim 2 wherein the liquid medium is selected from water, organic solvents, silicone solvents, chlorinated solvents and mixtures thereof.

5. A method according to claim 4 wherein the liquid medium comprises a sensor-compatible amount of a soil-sensing promoter selected from surfactants and emulsifiers and mixtures thereof.

6. A method according to claim 2 wherein the soil sensing means have one or more pair-wise correlation coefficients in the range from about 0.05 to about 0.75.

7. A method according to claim 2 wherein the model algorithm is developed using a plurality of soil sensors appropriate to a heterogeneous mixture of soils selected from greasy/oily, particulate, enzyme-sensitive, bleachable soils, burnt- and baked-on soils, body soils, environmental soils from smoke, grass, etc, incidental soils including food stains etc, applied soils from cosmetics and haircare products, cooking soils, and mixtures thereof.

8. A method according to claim 2 wherein the soil parameters are selected from turbidity, conductivity, pH, surface-tension, refractive index, ionic strength, heat capacity, viscosity, thermal conductivity, coefficient of expansion, dipole moment, adsorption, density, hydrophobicity, optical density, osmosis, optical activity, water-hardness and combinations thereof.

9. A method according to claim 8 wherein the soil parameters comprise a combination of turbidity and conductivity.

10. A method according to claim 2 wherein the model algorithm is a linear regression model, a non-linear regression model, a fuzzy logic model, a neural network model, a neuro-fuzzy network model, or a basis vector model.

11. A method according to claim 10 wherein the model algorithm is a regression model defined on the basis of one or more regression equations, at least one for each soil-sensing means, relating the experimental or consumer-generated soil parameter information to known soil concentration levels and providing best-fit estimates of regression coefficients and corresponding probability distribution functions.

12. A method according to claim 11 wherein the one or more regression equations of soil parameter on soil concentration is linear or linearizable by appropriate transformation with a standard deviation for the regression coefficient of less than about 40%.

13. A method according to claim 12 wherein the model algorithm is at least partly defined on the basis of one or more experimental or consumer-generated soil parameter datasets, p, q, etc, at least one for each sensing means, which have been transformed by offsetting with corresponding measurements under soil-free conditions $p^0$, $q^0$, etc so to provide offset soil parameter datasets $(p-p^0)$, $(q-q^0)$, etc.

14. A method according to any of claim 13 wherein the soil parameter datasets are further transformed by normalizing the offset soil parameter dataset $(p-p^0)$, etc against the maximum value of experimental or consumer-generated soil parameter measurements, $p_{max}$ etc in the corresponding offset soil parameter dataset so as to provide the normalized soil parameter dataset $p''$, $q''$ etc, where $p''=(p-p^0)/p_{max}$ and $p_{max}$ is the upper n %-ile value of $(p-p^0)$ in the corresponding offset soil parameter dataset and n lies in the range from about 80 to about 99.

15. A method according to claim 14 wherein the data processing step includes the step of transforming the soil parameter measurements for the or each sensing means, $p_j$, $q_j$ etc by offsetting with corresponding measurements of the liquid medium under soil-free conditions, $p_j^0$, $q_j^0$ etc to provide offset soil parameter measurements $(p_j-p_j^0)$, $(q_j-q_j^0)$ etc.

16. A method according to claim 15 wherein the soil parameter measurements are further transformed by normalizing the offset soil parameter measurements $(p_j-p_j^0)$ etc against the maximum value of experimental or consumer-generated soil parameter measurements $p_{max}$ in the corresponding offset soil parameter dataset so as to generate normalised soil parameter measurements $p_j''$, $q_j''$ etc.

17. A method according to claim 16 wherein the model algorithm generates a predicted soil probability distribution on the basis of 1) the soil parameter input data, the soil concentration versus soil parameter regression coefficients $(m_p)$ and the maximum value of soil concentration $s_{max}$ in the algorithm dataset, $s_{max}$ being the upper n %-ile value of soil concentration in the algorithm dataset wherein n lies in the range from about 80 to about 99; and/or 2) the normalised regression coefficients $(m_p'')$, $p_{max}$ and the normalised soil parameter measurements $(p_j'')$, and wherein the predicted soil probability distribution is a sum or weighted sum of terms in respect of each soil parameter.

18. A method according to claim 17 additionally comprising a soil category decision step wherein the soil in the liquid medium is assigned to an optimum one of a plurality of discrete soil category bands on the basis of the predicted soil probability distributions for the or each soil sensing means.

19. A method according to claim 18 wherein the plurality of discrete soil category bands are defined on the basis of the maximum value of soil concentration $s_{max}$ in the algorithm dataset and product-specific recommended usage data.

20. A method according to claim 19 wherein the optimum soil category band is assigned on the basis of one or more overlap functions between 1) the predicted soil probability distributions $(S_{p,j}, S_{q,j}$ etc) for each soil sensing means and the normalised soil category bands $(s_\mu'')$; and/or 2) the normalised predicted soil probability distributions $(S_{p,j}'', S_{q,j}''$ etc) for each soil sensing means and the soil category bands expressed in normalised parameter form $(s_{p,\mu}'', s_{q,\mu}''$ etc), the optimum soil category being a sum or weighted sum of the overlap functions in respect of each soil parameter.

21. A method according to claim 10 wherein the model algorithm is a basis vector model wherein the predicted soil data is represented as a linear combination of soil fractions each associated with a corresponding soil-sensing means and defined by reference to a standard model soil and wherein the soil fractions are combined in relative proportions dependent upon one or more weighting factors including the measured concentration of the soil fraction in the wash liquor or other liquid medium $(\kappa_{p,j})$.

22. A method according to claim 21 wherein the predicted soil data is represented by a linear combination of soil fractions including one fraction associated with a conductivity-based sensor (c-soil) and one fraction associated with a turbidity-based sensor (t-soil) with weighting factors dependent upon the measured concentrations of c-soil $(\kappa_{c,j})$ and t-soil $(\kappa_{t,j})$ in the wash liquor or other liquid medium.

23. A method according to claim 22 including the step of issuing one or more signals dependent upon one or more of $\kappa_{c,j}$, $\kappa_{t,j}$, $\kappa_{c,j}$:$\kappa_{t,j}$, T/C or some other function dependent upon turbidity/conductivity proportionality, to an output device, data store, user interface, data processor, or an appliance director or module for purposes of controlling a cleaning or washing process, wherein T is the offset soil parameter measurement for the turbidity-based sensor $(t_j-t_j^0)$ and C is the offset conductivity soil parameter measurement for the conductivity-based sensor $(c_j-c_j^0)$.

24. A method for measuring a degree of soiling of a soiled article or for cleaning the soiled article in a wash liquor or other liquid medium, the method comprising;
 a) a wetting step wherein the soiled article is brought into contact with a liquid medium to initiate removal of soil from the soiled article;
 b) a soil sensing step wherein the soil-containing liquid medium is contacted with a plurality of soil-sensing means each responsive to a distinct physico-chemical soil characteristic and providing one or more soil parameter measurements corresponding thereto, said plurality of soil sensing means including at least a conductivity-based sensor and a turbidity-based sensor;
 c) a data processing step wherein the soil parameter measurements for each sensing means are entered as input data into a model algorithm which functions to generate predicted soil data of enhanced confidence level;
 d) a communication step wherein one or more signals dependent upon the predicted soil data is issued to an output device, data store, user interface, data processor or an appliance director or module; and optionally
 e) a cleaning step wherein the soiled article is treated with one or more detergent products of a type or amount determined prior to treatment in accord with the predicted soil data.

* * * * *